United States Patent
Knerr

(10) Patent No.: US 9,655,339 B2
(45) Date of Patent: May 23, 2017

(54) LETTUCE NAMED GIMLET

(71) Applicant: SHAMROCK SEED COMPANY, INC., Salinas, CA (US)

(72) Inventor: Larry Knerr, Hollister, CA (US)

(73) Assignee: Shamrock Seed Company, Inc., Salinas, CA (US)

( * ) Notice: Subject to any disclaimer, the term of this patent is extended or adjusted under 35 U.S.C. 154(b) by 147 days.

(21) Appl. No.: 14/577,270

(22) Filed: Dec. 19, 2014

(65) Prior Publication Data

US 2015/0201575 A1  Jul. 23, 2015

Related U.S. Application Data

(60) Provisional application No. 61/929,606, filed on Jan. 21, 2014.

(51) Int. Cl.
*A01H 5/12* (2006.01)

(52) U.S. Cl.
CPC ...................... *A01H 5/12* (2013.01)

(58) Field of Classification Search
None
See application file for complete search history.

(56) References Cited

U.S. PATENT DOCUMENTS

| | | | |
|---|---|---|---|
| 5,304,719 A | 4/1994 | Segebart | |
| 5,367,109 A | 11/1994 | Segebart | |
| 5,523,520 A | 6/1996 | Hunsperger et al. | |
| 5,684,226 A | 11/1997 | Sarreal | |
| 5,850,009 A | 12/1998 | Kevern | |
| 5,968,830 A | 10/1999 | Dan et al. | |
| 6,555,735 B2 | 4/2003 | Sarreal | |
| 7,102,060 B1 | 9/2006 | Knerr | |
| 7,119,257 B1 | 10/2006 | Schuitman | |
| 7,126,045 B2 | 10/2006 | Knerr | |
| 7,314,976 B1 | 1/2008 | Knerr | |
| 7,314,977 B1 | 1/2008 | Knerr | |
| 7,314,978 B1 | 1/2008 | Knerr | |
| 7,321,078 B1 | 1/2008 | Knerr | |
| 7,326,829 B1 | 2/2008 | Knerr | |
| 7,332,653 B2 | 2/2008 | Knerr | |
| 7,332,654 B1 | 2/2008 | Knerr | |
| 7,342,149 B2 | 3/2008 | Knerr | |
| 7,345,223 B1 | 3/2008 | Knerr | |
| 7,371,929 B2 | 5/2008 | Knerr | |
| 7,371,930 B1 | 5/2008 | Knerr | |
| 7,371,931 B1 | 5/2008 | Knerr | |
| 7,371,932 B1 | 5/2008 | Knerr | |
| 7,371,933 B1 | 5/2008 | Knerr | |
| 7,453,026 B1 | 11/2008 | Knerr | |
| 7,453,027 B1 | 11/2008 | Knerr | |
| 7,459,606 B1 | 12/2008 | Knerr | |
| 7,572,954 B2 | 8/2009 | Knerr | |
| 7,579,519 B1 | 8/2009 | Knerr | |
| 7,579,520 B1 | 8/2009 | Knerr | |
| 7,579,521 B1 | 8/2009 | Knerr | |
| 7,592,510 B2 | 9/2009 | Knerr | |
| 7,598,433 B1 | 10/2009 | Knerr | |
| 7,626,085 B2 | 12/2009 | Knerr | |
| 7,960,617 B2 | 6/2011 | Knerr | |
| 8,076,539 B2 | 12/2011 | Knerr | |
| 8,106,262 B2 | 1/2012 | Michel | |
| 8,106,263 B2 | 1/2012 | Knerr | |
| 8,148,610 B2 | 4/2012 | Knerr | |
| 8,309,797 B2 | 11/2012 | Bellec | |
| 8,362,326 B2 | 1/2013 | Bellec | |
| 8,399,741 B2 | 3/2013 | Knerr | |
| 8,481,817 B2 * | 7/2013 | Knerr | A01H 5/12 435/410 |
| 8,481,818 B2 | 7/2013 | Knerr | |
| 8,487,161 B2 | 7/2013 | Knerr | |
| 8,546,649 B2 | 10/2013 | Knerr | |

OTHER PUBLICATIONS

U.S. Appl. No. 12/450,026, filed Dec. 2, 2010, Michel, H.
U.S. Appl. No. 13/353,475, filed May 10, 2012, Knerr L.
U.S. Appl. No. 13/351,164, filed May 10, 2012, Knerr L.
U.S. Appl. No. 11/858,813, filed Mar. 27, 2008, Knerr L.
Allard, 1960. Principle of Plant Breeding. John Wiley & Sons, Inc. p. 55.
Bassett, et al., 1975. The Role of Leaf Shape in the Inheritance of Heading in Lettuce. J. Amer. Soc. Hort. Sci. 100(2):104-105.
Bassett, et al., 1999. Allelism Found between Two Common Bean Genes, Hilum Ring Color (D) and Partly Colored Seedcoat Pattern (Z), formely Assumed to be Independent. J. Amer. Hort. Sci. 124 (6): 649-653.
Darnell, et al., 1990. DNA Replication, Repair and Recombination. In Molecular Cell Biology, 2nd edition, W.H. Freeman and Co., p. 478.
Eshed, et al., 1996. Less-Than-Additive Epistatic Interactions of Quatitative Trait Loci in Tomato. Genetics 143:1807-1817.
Kraft, et al., 2000. Linkage Desequilibrium and Fingerprinting in Sugar Beet. Theor. Appl. Genet. 101:323-326.
Poehlman, J.M. and Sleeper, D.A., Methods in Plant Breeding. In Breeding Field Crops, 5th ed. (2006), Iowa State University Press, pp. 171-183.
Waycott et al., 1994. Differentiation of nearly identical germplasm accessions by a combination of molecular and morphologic analyse. In Genome 37(4):577-583.
Ryder et al., 1992. Lettuce genetics: inheritance, linkage and epistasis. In J. Amer. Soc. Hort. Sci. 117(3): 504-507.
Ryder et al., 1999. Inheritance and epistasis studies of chlorophyll deficiency in lettuce. In J. Amer. Soc. Hort. Sci. 124(6): 636-640.
Michelmore et al., 1987.Transformation of lettuce (lactuca sativa) mediated by agrobacterium tumefaciens. In Plant Cell Rep. 6:439-442.
Xinrun and Conner. 1992. Genotypic effects on tissue culture response of lettuce cotyledons. In J. Genet. & Breed 46:287-290.

\* cited by examiner

*Primary Examiner* — Ashley K Buran
(74) *Attorney, Agent, or Firm* — Cooley LLP

(57) ABSTRACT

Novel lettuce cultivar, designated GIMLET, is disclosed. The invention relates to the seeds of lettuce cultivar GIMLET, to the plants of lettuce line GIMLET, and to methods for producing a lettuce plant by crossing the cultivar GIMLET with itself or another lettuce line, respectively. The invention further relates to methods for producing a lettuce plant containing in its genetic material one or more transgenes and to the transgenic plants produced by that method and to methods for producing other lettuce lines derived from the cultivar GIMLET.

22 Claims, No Drawings

LETTUCE NAMED GIMLET

CROSS-REFERENCE TO RELATED APPLICATIONS

The present application claims priority to, and the benefit of U.S. Provisional Patent Application No. 61/929,606, filed Jan. 21, 2014, which is herein incorporated by reference in its entirety for all purposes.

FIELD OF THE INVENTION

The present invention relates to new and distinctive lettuce (*Lactuca sativa*) cultivars, designated SCARAMANGA, GIMLET, SPRITZER, and/or MOJITO.

BACKGROUND OF THE INVENTION

The disclosures, including the claims, figures and/or drawings, of each and every patent, patent application, and publication cited herein are hereby incorporated herein by reference in their entireties.

The following description includes information that may be useful in understanding the present invention. It is not an admission that any of the information provided herein is prior art or relevant to the presently claimed inventions, or that any publication specifically or implicitly referenced is prior art.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possesses the traits to meet the program goals. The goal is to combine in a single variety an improved combination of desirable traits from the parental germplasm.

In lettuce, these important traits may include increased head size and weight, higher seed yield, improved color, resistance to diseases and insects, tolerance to drought and heat, better post-harvest shelf-life of the leaves, better standing ability in the field, better uniformity, and better agronomic quality.

Most cultivated forms of lettuce belong to the highly polymorphic species *Lactuca sativa* which is grown for its edible head and leaves. As a crop, lettuce is grown commercially wherever environmental conditions permit the production of an economically viable yield. Lettuce is the world's most popular salad. In the United States, the principal growing regions are California and Arizona which produce approximately 329,000 acres out of a total annual acreage of more than 333,000 acres (USDA, 2005). Fresh lettuce is available in the United States year-round although the greatest supply is from May through October. For planting purposes, the lettuce season is typically divided into three categories, early, mid and late, with the coastal areas planting from January to August, and the desert regions from August to December. Lettuce is consumed nearly exclusively as fresh, raw product, and occasionally as a cooked vegetable. Baby leaf or spring mix lettuce is an increasingly popular crop as worldwide baby leaf lettuce consumption continues to increase. Spring mix lettuce refers to lettuce that is grown in high concentrations and harvested at a very young or 'baby leaf' stage, typically 30 to 45 days after planting. The plantings are often done on wider 80 to 84 inch beds and often contain up to one million plants per acre. Compared to iceberg or romaine plantings, where they are typically harvested 60 to 100 days after planting, with a population of roughly 25,000 to 30,000 plants per acre. Spring mix plantings often include multiple types of lettuces, all harvested when the leaves are young and tender. These plantings can include green romaine, red romaine, dark lolla rossa, tango, green leaf, and red leaf types. Spring mix fields are most often harvested mechanically and the harvested leaves are packed in plastic totes, where they are transported to a processing facility where they are washed, processed and mixed according to the salad recipe.

*Lactuca sativa* is in the Cichoreae tribe of the Asteraceae (Compositae family). Lettuce is related to chicory, sunflower, aster, dandelion, artichoke, and *chrysanthemum*. *Sativa* is one of about 300 species in the genus *Lactuca*. There are several morphological types of lettuce. The Crisphead group includes the Iceberg and Batavian types. Iceberg lettuce has a large, firm head with a crisp texture and a white or creamy yellow interior. Batavian lettuce predates Iceberg lettuce and has a smaller and less firm head. The Butterhead group has a small, soft head with an almost oily texture. Romaine lettuce, also known as Cos lettuce, has elongated upright leaves forming a loose, loaf-shaped head and the outer leaves are usually dark green. Leaf lettuce comes in many varieties, none of which form a head. There are three types of lettuce which are seldom seen in the United States: Latin lettuce, which looks like a cross between Romaine and Butterhead; Stem lettuce, which has long, narrow leaves and thick, edible stems; and Oilseed lettuce, which is a primitive type of lettuce grown for its large seeds that are pressed to obtain oil.

*Lactuca sativa* is a simple diploid species with nine pairs of chromosomes (2N=18). Lettuce is an obligate self-pollinating species which means that pollen is shed before stigma emergence, assuring 100% self-fertilization. Since each lettuce flower is an aggregate of about 10-20 individual florets (typical of the Compositae family), manual removal of the anther tubes containing the pollen is tedious. As a result, a modified method of misting to wash off the pollen prior to fertilization is needed to assure crossing or hybridization. Flowers to be used for crossings are selected about 60-90 minutes after sunrise. Selection criteria include plants with open flowers, where the stigma has emerged and pollen is visibly attached to a single stigma (there are about 10-20 stigma). Pollen grains are washed off using 3-4 pumps of water from a spray bottle and with enough pressure to dislodge the pollen grains without damaging the style. Excess water is then dried off using clean paper towels and about 30 minutes later, the styles spring back up and the two lobes of the stigma are visibly open in a "V" shape. Pollen from another variety or donor parent is then introduced by gently rubbing the stigma and style of the donor parent to the maternal parent. Most pertinent information including dates and pedigree are then secured to the flowers using tags.

Choice of breeding or selection methods depends on the mode of plant reproduction, the heritability of the trait(s) being improved, and the type of cultivar used commercially (e.g., $F_1$ hybrid cultivar, pure line cultivar, etc.). For highly heritable traits, a choice of superior individual plants evaluated at a single location may be effective, whereas for traits with low heritability, selection should be based on mean values obtained from replicated evaluations of families of related plants. Popular selection methods commonly include pedigree selection, modified pedigree selection, mass selection, recurrent selection and backcross breeding.

The complexity of inheritance influences choice of the breeding method. Backcross breeding is used to transfer one or a few favorable genes for a highly heritable trait into a desirable cultivar. This approach has been used extensively for breeding disease-resistant cultivars. Nevertheless, it is also suitable for the adjustment and selection of morphological character, color characteristics and simply inherited quantitative characters. Various recurrent selection techniques are used to improve quantitatively inherited traits controlled by numerous genes. The use of recurrent selection in self-pollinating crops depends on the ease of pollination, the frequency of successful hybrids from each pollination and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars. Those still deficient in a few traits may be used as parents to produce new populations for further selection.

These processes, which lead to the final step of marketing and distribution, usually take from eight to twelve years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and/or to a widely grown standard cultivar. If a single observation is inconclusive, replicated observations provide a better estimate of its genetic worth.

The goal of lettuce plant breeding is to develop new, unique and superior lettuce cultivars. The breeder initially selects and crosses two or more parental lines, followed by repeated selfing and selection, producing many new genetic combinations. Another method used to develop new and unique lettuce cultivar occurs when the lettuce breeder selects and crosses parental varieties followed by haploid induction and chromosome doubling that result in the development of dihaploid cultivars. The breeder can theoretically generate billions of different genetic combinations via crossing, selfing and mutations and the same is true for the utilization of the dihaploid breeding method.

Each year, the plant breeder selects the germplasm to advance to the next generation. This germplasm is grown under unique and different geographical, climatic and soil conditions and further selections are then made during and at the end of the growing season. The cultivars that are developed are unpredictable. This unpredictability is because the breeder's selection occurs in unique environments with no control at the DNA level (using conventional breeding procedures or dihaploid breeding procedures), and with millions of different possible genetic combinations being generated. A breeder of ordinary skill in the art cannot predict the final resulting lines he develops, except possibly in a very gross and general fashion. This unpredictability results in the expenditure of large amounts of research monies to develop superior new lettuce cultivars.

The development of new lettuce cultivars requires the development and selection of lettuce varieties, the crossing of these varieties and the evaluation of the crosses.

Pedigree breeding and recurrent selection breeding methods are used to develop cultivars from breeding populations. Breeding programs combine desirable traits from two or more cultivars or various broad-based sources into breeding pools from which cultivars of desired phenotypes are developed by selfing and selection or through the dihaploid breeding method.

Pedigree breeding is used commonly for the improvement of self-pollinating crops or inbred lines of cross-pollinating crops. Two parents that possess favorable, complementary traits are crossed to produce an $F_1$. An $F_2$ population is produced by selfing one or several $F_1$s or by intercrossing two $F_1$s (sib mating). The dihaploid breeding method could also be used. Selection of the best individuals may begin in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified, or created, by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, lettuce breeders commonly harvest one or more flower containing seed from each plant in a population and thresh them together to form a bulk. Part of the bulk is used to plant the next generation and part is put in reserve. The procedure has been referred to as modified single-seed descent or the bulk technique.

The multiple-seed procedure has been used to save labor at harvest. It is considerably faster than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs-which are also referred to as Microsatellites), and Single Nucleotide Polymorphisms (SNPs).

Isozyme Electrophoresis and RFLPs have been widely used to determine genetic composition. Shoemaker and Olsen (Molecular Linkage Map of Soybean (*Glycine max*), pp. 6.131-6.138 in S. J. O'Brien (ed.) Genetic Maps: Locus Maps of Complex Genomes, Cold Spring Harbor Laboratory Press, Cold Spring Harbor, N.Y. (1993)) developed a molecular genetic linkage map that consisted of 25 linkage groups with about 365 RFLP, 11 RAPD, three classical markers, and four isozyme loci. See also, Shoemaker, R. C., RFLP Map of Soybean, pp. 299-309, in Phillips, R. L. and Vasil, I. K. (eds.), DNA-Based Markers in Plants, Kluwer Academic Press, Dordrecht, the Netherlands (1994).

SSR technology is an efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. Diwan, N. and Cregan, P. B., Theor. Appl. Genet., 95:22-225 (1997). SNPs may also be used to identify the unique genetic composition of the invention and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection.

Molecular markers may also be used to identify and exclude certain sources of germplasm as parental varieties or ancestors of a plant by providing a means of tracking genetic profiles through crosses.

Mutation breeding is another method of introducing new traits into lettuce varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid, or acridines. Once a desired trait is observed through mutagenesis the trait may then be incorporated into existing germplasm by traditional breeding techniques. Details of mutation breeding can be found in Principles of Cultivar Development by Fehr, Macmillan Publishing Company (1993). The production of double haploids can also be used for the development of homozygous varieties in a breeding program. Double haploids are produced by the doubling of a set of chromosomes from a heterozygous plant to produce a completely homozygous individual. For example, see Wan, et al., Theor. Appl. Genet., 77:889-892 (1989).

Descriptions of other breeding methods that are commonly used for different traits and crops can be found in one of several reference books (e.g., R. W. Allard, 1960, Principles of Plant Breeding, John Wiley and Son, pp. 115-161; N. W. Simmonds, 1979, Principles of Crop Improvement, Longman Group Limited; W. R. Fehr, 1987, Principles of Crop Development, Macmillan Publishing Co.; N. F. Jensen, 1988, Plant Breeding Methodology, John Wiley & Sons).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Lettuce is an important and valuable vegetable crop. Thus, a continuing goal of plant breeders is to develop stable, high yielding lettuce cultivars that are agronomically sound. The reasons for this goal are obviously to maximize the amount of yield produced on the land. To accomplish this goal, the lettuce breeder must select and develop lettuce plants that have the traits that result in superior cultivars.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary, not limiting in scope. In various embodiments, one or more of the above-described problems have been reduced or eliminated, while other embodiments are directed to other improvements.

According to the invention, there is provided four novel lettuce cultivars designated SCARAMANGA, GIMLET, SPRITZER and/or MOJITO. This invention thus relates to the seeds of lettuce cultivars SCARAIVIANGA, GIMLET, SPRITZER and/or MOJITO, to the plants, or part(s) thereof of lettuce cultivars SCARAIVIANGA, GIMLET, SPRITZER and/or MOJITO, to plants or part(s) thereof consisting essentially of the phenotypic and morphological characteristics of lettuce cultivars SCARAIVIANGA, GIMLET, SPRITZER and/or MOJITO, and/or having all the phenotypic and morphological characteristics of lettuce cultivars SCARAMANGA, GIMLET, SPRITZER and/or MOJITO, and/or having the phenotypic and morphological characteristics of lettuce cultivars SCARAMANGA, GIMLET, SPRITZER and/or MOJITO listed in Tables 1 to 4, including but not limited to as determined at the 5% significance level when grown in the same environmental conditions. The invention also relates to variants, mutants and trivial modifications of the seed or plant of lettuce cultivars SCARAMANGA, GIMLET, SPRITZER and/or MOJITO. Plant parts of the lettuce cultivars of the present invention are also provided such as, i.e., pollen obtained from the plant cultivars and an ovule obtained from the plant cultivars.

The plants and seeds of the present invention include those that may be of an essentially derived variety as defined in section 41(3) of the Plant Variety Protection Act, i.e., a variety that:
  (i) is predominantly derived from lettuce cultivars SCARAMANGA, GIMLET, SPRITZER and/or MOJITO or from a variety that is predominantly derived from lettuce cultivars SCARAMANGA, GIMLET, SPRITZER and/or MOJITO, while retaining the expression of the essential characteristics that result from the genotype or combination of genotypes of lettuce cultivars SCARAIVIANGA, GIMLET, SPRITZER and/or MOJITO;
  (ii) is clearly distinguishable from lettuce cultivars SCARAMANGA, GIMLET, SPRITZER and/or MOJITO; and
  (iii) except for differences that result from the act of derivation, conforms to the initial variety in the expression of the essential characteristics that result from the genotype or combination of genotypes of the initial variety.

In another aspect, the present invention provides regenerable cells for use in tissue culture of lettuce cultivars SCARAIVIANGA, GIMLET, SPRITZER and/or MOJITO. The tissue culture will preferably be capable of regenerating plants consisting essentially of the phenotypic and morphological characteristics of lettuce cultivars SCARAMANGA, GIMLET, SPRITZER and/or MOJITO, and/or having all the phenotypic and morphological characteristics of lettuce cultivars SCARAMANGA, GIMLET, SPRITZER and/or MOJITO, and/or having the physiological and morphological characteristics of lettuce cultivars SCARAMANGA, GIMLET, SPRITZER and/or MOJITO listed in Tables 1 to 4, including but not limited to as determined at the 5% significance level when grown in the same environmental conditions. Preferably, the cells of such tissue culture will be embryos, meristematic cells, seeds, callus, pollen, leaves, anthers, pistils, roots, root tips, flowers, stems and axillary buds. Protoplasts produced from such tissue culture are also included in the present invention. The lettuce shoots, roots and whole plants regenerated from the tissue culture are also part of the invention.

Also included in the invention are methods for producing a lettuce plant produced by crossing lettuce cultivars SCARAMANGA, GIMLET, SPRITZER and/or MOJITO, respectively with itself or another lettuce cultivar. When crossed with itself, i.e., when SCARAMANGA is crossed with another lettuce cultivar SCARAMANGA plant or self-pollinated, when GIMLET, is crossed with another lettuce cultivar GIMLET plant or self-pollinated, when SPRITZER is crossed with another lettuce cultivar SPRITZER plant or self-pollinated, when MOJITO is crossed with another lettuce cultivar MOJITO plant or self-pollinated, lettuce cultivar SCARAMANGA, GIMLET, SPRITZER and/or MOJITO, respectively will be conserved (e.g., as an inbred). When crossed with another, different lettuce plant, an $F_1$ hybrid seed is produced. $F_1$ hybrid seeds and plants produced by growing said hybrid seeds are included in the present invention. A method for producing an $F_1$ hybrid lettuce seed comprising crossing a lettuce cultivar SCARAMANGA, GIMLET, SPRITZER and/or MOJITO plant with a different lettuce plant and harvesting the resultant hybrid lettuce seed are also part of the invention. The hybrid lettuce seed produced by the method comprising crossing a lettuce cultivar SCARAIVIANGA, GIMLET, SPRITZER and/or MOJITO plant with a different lettuce plant and harvesting the resultant hybrid lettuce seed, are included in the invention, as are the hybrid lettuce plant, or part(s) thereof, and seeds produced by growing said hybrid lettuce seed.

In another aspect, the present invention provides transformed SCARAMANGA, GIMLET, SPRITZER and/or MOJITO lettuce cultivar plants or part(s) thereof that have been transformed so that its genetic material contains one or more transgenes, preferably operably linked to one or more regulatory elements. Also, the invention provides methods for producing a lettuce plant containing in its genetic material one or more transgenes, preferably operably linked to one or more regulatory elements, by crossing transformed SCARAIVIANGA, GIMLET, SPRITZER and/or MOJITO lettuce cultivar plants with either a second plant of another lettuce cultivar, or a non-transformed SCARAMANGA, GIMLET, SPRITZER and/or MOJITO lettuce cultivar, so that the genetic material of the progeny that results from the cross contains the transgene(s), preferably operably linked to one or more regulatory elements. The invention also provides methods for producing a lettuce plant that contains in its genetic material one or more transgene(s), wherein the method comprises crossing the cultivars SCARAMANGA, GIMLET, SPRITZER and/or MOJITO with a second lettuce cultivar of another lettuce cultivar which contains one or more transgene(s) operably linked to one or more regulatory element(s) so that the genetic material of the progeny that results from the cross contains the transgene(s) operably linked to one or more regulatory element(s). Transgenic lettuce cultivars, or part(s) thereof produced by the methods are in the scope of the present invention.

More specifically, the invention comprises methods for producing a male sterile lettuce plant, an herbicide resistant lettuce plant, an insect resistant lettuce plant, a disease resistant lettuce plant, a water stress tolerant lettuce plant, a heat stress tolerant lettuce plant, and a lettuce plant with improved shelf-life and a lettuce plant with delayed senescence. Said methods comprise transforming lettuce cultivars SCARAMANGA, GIMLET, SPRITZER and/or MOJITO plant with a nucleic acid molecule that confers, for example, male sterility, herbicide resistance, insect resistance, disease resistance, water stress tolerance, heat stress tolerance, improved shelf life or delayed senescence respectively. The transformed lettuce plants, or part(s) thereof, obtained from the provided methods, including, for example, a male sterile lettuce plant, an herbicide resistant lettuce plant, an insect resistant lettuce plant, a disease resistant lettuce plant, a lettuce plant tolerant to water stress, a lettuce plant tolerant to heat stress, a lettuce plant with improved shelf-life, a lettuce plant with improved shelf-life and delayed senescence are included in the present invention. For the present invention and the skilled artisan, disease is understood to be fungal diseases, viral diseases, bacterial diseases or other plant pathogenic diseases and a disease resistant plant will encompass a plant resistant to fungal, viral, bacterial and other plant pathogens.

In another aspect, the present invention provides for methods of introducing one or more desired trait(s) into lettuce cultivars SCARAIVIANGA, GIMLET, SPRITZER and/or MOJITO and plants obtained from such methods. The desired trait(s) may be, but not exclusively, a single gene, preferably a dominant but also a recessive allele. Preferably, the transferred gene or genes will confer such traits as male sterility, herbicide resistance, insect resistance, resistance to bacterial, fungal, or viral disease, increased leaf number, improved shelf-life, delayed senescence and tolerance to water stress or heat stress. The gene or genes may be naturally occurring gene(s) or transgene(s) introduced through genetic engineering techniques. The method for introducing the desired trait(s) is preferably a backcrossing process making use of a series of backcrosses to lettuce cultivars SCARAIVIANGA, GIMLET, SPRITZER and/or MOJITO during which the desired trait(s) is maintained by selection.

When using a transgene, the trait is generally not incorporated into each newly developed line/cultivar such as lettuce cultivars SCARAMANGA, GIMLET, SPRITZER and/or MOJITO by direct transformation. Rather, the more typical method used by breeders of ordinary skill in the art to incorporate the transgene is to take a line already carrying the transgene and to use such line as a donor line to transfer the transgene into the newly developed line. The same would apply for a naturally occurring trait or one arising from spontaneous or induced mutations. The backcross breeding process of SCARAIVIANGA comprises the following steps: (a) crossing lettuce cultivar SCARAMANGA plants with plants of another cultivar that comprise the desired trait(s); (b) selecting the $F_1$ progeny plants that have the desired trait(s); (c) crossing the selected $F_1$ progeny plants with lettuce cultivar SCARAIVIANGA plants to produce backcross progeny plants; (d) selecting for backcross progeny plants that have the desired trait(s) and physiological and morphological characteristics of lettuce cultivar SCARAMANGA to produce selected backcross progeny plants; and (e) repeating steps (c) and (d) one, two, three, four, five six, seven, eight, nine, or more times in succession to produce selected, second, third, fourth, fifth, sixth, seventh, eighth, ninth, or higher backcross progeny plants that consist essentially of the phenotypic and morphological characteristics of lettuce cultivar SCARAIVIANGA, and/or have all the phenotypic and morphological characteristics of lettuce cultivar SCARAIVIANGA, and/or have the desired trait(s) and the physiological and morphological characteristics of lettuce cultivar SCARAIVIANGA as determined in Table 1, including but not limited to at a 5% significance level when grown in the same environmental conditions. The backcross breeding process of GIMLET comprises the following steps: (a) crossing lettuce cultivar GIMLET plants with plants of another cultivar that comprise the desired trait(s); (b) selecting the $F_1$ progeny plants that have the desired trait(s); (c) crossing the selected $F_1$ progeny plants with lettuce cultivar GIMLET plants to produce backcross progeny plants; (d) selecting for backcross progeny plants that have the desired trait(s) and physiological and morphological characteristics of lettuce cultivar GIMLET to produce selected backcross progeny plants; and (e) repeating steps (c) and (d) one, two, three, four, five six, seven, eight, nine, or more times in succession to produce selected, second, third, fourth, fifth, sixth, seventh, eighth, ninth, or higher backcross progeny plants that consist essentially of the phenotypic and morphological characteristics of lettuce cultivar GIMLET, and/or have all the phenotypic and morphological characteristics of lettuce cultivar GIMLET, and/or have the desired trait(s) and the physiological and morphological characteristics of lettuce cultivar GIMLET as determined in Table 2, including but not limited to at a 5% significance level when grown in the same environmental conditions. The backcross breeding process of SPRITZER comprises the following steps: (a) crossing lettuce cultivar SPRITZER plants with plants of another cultivar that comprise the desired trait(s); (b) selecting the $F_1$ progeny plants that have the desired trait(s); (c) crossing the selected $F_1$ progeny plants with lettuce cultivar SPRITZER plants to produce backcross progeny plants; (d) selecting for backcross progeny plants that have the desired trait(s) and physiological and morphological characteristics of lettuce cultivar SPRITZER to produce selected backcross progeny plants; and (e) repeating steps (c) and (d) one, two, three, four, five six, seven, eight, nine, or more times in succession to produce selected, second, third, fourth, fifth, sixth, seventh, eighth, ninth, or higher backcross progeny plants that consist essentially of the phenotypic and morphological characteristics of lettuce cultivar SPRITZER, and/or have all the phenotypic and morphological characteristics of lettuce cultivar SPRITZER, and/or have the desired trait(s) and the physiological and morphological characteristics of lettuce cultivar SPRITZER as determined in Table 3, including but not limited to at a 5% significance level when grown in the same environmental conditions. The backcross breeding process of MOJITO comprises the following steps: (a) crossing lettuce cultivar MOJITO plants with plants of another cultivar that comprise the desired trait(s); (b) selecting the $F_1$ progeny plants that have the desired trait(s); (c) crossing the selected $F_1$ progeny plants with lettuce cultivar MOJITO plants to produce backcross progeny plants; (d) selecting for backcross progeny plants that have the desired trait(s) and physiological and morphological characteristics of lettuce cultivar MOJITO to produce selected backcross progeny plants; and (e) repeating steps (c) and (d) one, two, three, four, five six, seven, eight, nine, or more times in succession to produce selected, second, third, fourth, fifth, sixth, seventh, eighth, ninth, or higher backcross progeny plants that consist essentially of the phenotypic and morphological characteristics of lettuce cultivar MOJITO, and/or have all the phenotypic and morphological characteristics of lettuce cultivar MOJITO, and/or have the desired trait(s) and the physiological and morphological characteristics of lettuce cultivar MOJITO as determined in Table 4, including but not limited to at a 5% significance level when grown in the same environmental conditions. The lettuce plants produced by the methods are also part of the invention. Backcrossing breeding methods, well-known for one skilled in the art of plant breeding, will be further developed in subsequent parts of the specification.

In a preferred embodiment, the present invention provides methods for increasing and producing lettuce cultivar SCARAIVIANGA, GIMLET, SPRITZER and/or MOJITO seed, whether by crossing a first parent lettuce cultivar plant with a second parent lettuce cultivar plant and harvesting the resultant lettuce seed, wherein both said first and second parent lettuce cultivar plant are the lettuce cultivars SCARAMANGA, GIMLET, SPRITZER and/or MOJITO, respectively or by planting a lettuce seed of the lettuce cultivars SCARAMANGA, GIMLET, SPRITZER and/or MOJITO, growing a lettuce cultivar SCARAIVIANGA, GIMLET, SPRITZER and/or MOJITO plant from said seed, respectively, controlling a self pollination of the plant where the pollen produced by a grown lettuce cultivar SCARAIVIANGA plant pollinates the ovules produced by the very same lettuce cultivar SCARAIVIANGA grown plant, where the pollen produced by a grown lettuce cultivar GIMLET plant pollinates the ovules produced by the very same lettuce cultivar GIMLET grown plant, where the pollen produced by a grown lettuce cultivar SPRITZER plant pollinates the ovules produced by the very same lettuce cultivar SPRITZER grown plant, where the pollen produced by a grown lettuce cultivar MOJITO plant pollinates the ovules produced by the very same lettuce cultivar MOJITO grown plant, and harvesting the resultant seed.

The invention further provides methods for developing lettuce cultivars in a lettuce breeding program using plant breeding techniques including recurrent selection, backcrossing, pedigree breeding, molecular markers (Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs). Amplified Fragment Length Polymorphisms (AFLPs), and Simple Sequence Repeats (SSRs) which are also referred to as Microsatellites, etc.) enhanced selection, genetic marker enhanced selection, and transformation. Seeds, lettuce plants, and part(s) thereof produced by such breeding methods are also part of the invention.

In addition to the exemplary aspects and embodiments described above, further aspects and embodiments will become apparent by study of the following descriptions.

DEFINITIONS

In the description and tables that follow, a number of terms are used. In order to provide a clear and consistent understanding of the specification and claims, including the scope to be given such terms, the following definitions are provided:

Allele. An allele is any of one or more alternative forms of a gene which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotypes of the $F_1$ hybrid.

Big Vein virus. Big vein is a disease of lettuce caused by Lettuce Mirafiori Big Vein Virus which is transmitted by the fungus *Olpidium virulentus*, with vein clearing and leaf shrinkage resulting in plants of poor quality and reduced marketable value.

Bolting. The premature development of a flowering stalk, and subsequent seed, before a plant produces a food crop. Bolting is typically caused by late planting when temperatures are low enough to cause vernalization of the plants.

*Bremia lactucae*. An Oomycete that causes downy mildew in lettuce in cooler growing regions.

Core length. Length of the internal lettuce stem measured from the base of the cut and trimmed head to the tip of the stem.

Corky root. A disease caused by the bacterium *Sphingomonas suberifaciens*, which causes the entire taproot to become brown, severely cracked, and non-functional.

Essentially all the physiological and morphological characteristics. A plant having essentially all the physiological and morphological characteristics means a plant having the physiological and morphological characteristics, except for the characteristics derived from the converted gene.

First water date. The date the seed first receives adequate moisture to germinate. This can and often does equal the planting date Head diameter. Diameter of the cut and trimmed head, sliced vertically, and measured at the widest point perpendicular to the stem.

Head height. Height of the cut and trimmed head, sliced vertically, and measured from the base of the cut stem to the cap leaf.

Head weight. Weight of saleable lettuce head, cut and trimmed to market specifications.

Immunity to disease(s) and or insect(s). A lettuce plant which is not subject to attack or infection by specific disease(s) and or insect(s) is considered immune.

Intermediate/Moderate resistance to disease(s) and or insect(s). A lettuce plant that restricts the growth and development of specific disease(s) and or insect(s), but may exhibit a greater range of symptoms or damage compared to high/standard resistant plants. Intermediate resistant plants will usually show less severe symptoms or damage than susceptible plant varieties when grown under similar environmental conditions and/or specific disease(s) and or insect(s) pressure, but may have heavy damage under heavy pressure. Intermediate resistant lettuce plants are not immune to the disease(s) and or insect(s).

Maturity Date. Maturity refers to the stage when plants are of full size or optimum weight, and in marketable form or shape to be of commercial or economic value. In leaf types they range from 50-75 days from time of seeding, depending upon the season of the year. In leaf types they range from 65-105 days from time of seeding, depending upon the season of the year Lettuce Mosaic virus. A disease that can cause a stunted, deformed, or mottled pattern in young lettuce and yellow, twisted, and deformed leaves in older lettuce.

Lettuce Yield (Tons/Acre). The yield in tons/acre is the actual yield of the lettuce at harvest.

*Nasonovia ribisnigri*. A lettuce aphid that colonizes the innermost leaves of the lettuce plant, contaminating areas that cannot be treated easily with insecticides.

Plant adaptability. A plant having good plant adaptability means a plant that will perform well in different growing conditions and seasons.

Plant cell. As used herein, the term "plant cell" includes plant cells whether isolated, in tissue culture, or incorporated in a plant or plant part.

Plant part. As used herein, the term "plant part" includes any part of the plant including but not limited to leaves, heads, stems, roots, seed, embryos, pollen, ovules, flowers, root tips, anthers, tissue, cells, axillary buds, and the like.

Ratio of head height/diameter. Head height divided by the head diameter is an indication of the head shape; <1 is flattened, 1=round, and >1 is pointed Regeneration. Regeneration refers to the development of a plant from tissue culture.

High/standard resistance to disease(s) and or insect(s). A lettuce plant that restricts highly the growth and development of specific disease(s) and or insect(s) under normal disease(s) and or insect(s) attack pressure when compared to susceptible plants. These lettuce plants can exhibit some symptoms or damage under heavy disease(s) and or insect(s) pressure. Resistant lettuce plants are not immune to the disease(s) and or insect(s).

RHS. RHS refers to the Royal Horticultural Society of England which publishes an official botanical color chart quantitatively identifying colors according to a defined numbering system. The chart may be purchased from Royal Hort. Society Enterprise Ltd. RHS Garden; Wisley, Woking, Surrey GU236QB, UK.

Single gene converted (conversion). Single gene converted (conversion) plants refer to plants which are developed by a plant breeding technique called backcrossing wherein essentially all of the desired morphological and physiological characteristics of a variety are recovered in addition to the single gene transferred into the variety via the backcrossing technique or via genetic engineering.

Susceptible to disease(s) and or insect(s). A lettuce plant that is susceptible to disease(s) and or insect(s) is defined as a lettuce plant that has the inability to restrict the growth and development of specific disease(s) and or insect(s). Plants that are susceptible will show damage when infected and are more likely to have heavy damage under moderate levels of specific disease(s) and or insect(s).

Tolerance to abiotic stresses. A lettuce plant that is tolerant to abiotic stresses such as, for example bolting or tipburn has the ability to endure abiotic stress without serious consequences for growth, appearance and yield.

Tip burn. Means a browning of the edges or tips of lettuce leaves that is a physiological response to a lack of calcium.

Tomato Bushy Stunt. A disease which causes stunting of growth, leaf mottling, and deformed or absent fruit.

DETAILED DESCRIPTION OF THE INVENTION

Lettuce cultivar SCARAMANGA has superior characteristics and was developed from an initial cross that was made in a greenhouse in Gilroy, Calif. during the first year of development under number 71030040, between red romaine and red little gem plants. The $F_1$ plants were grown in Gilroy, Calif. F2 and F3 were selected for color improvement and an F3 plant showing slower bolting was taken from the F3 population to produce an F4 seed. This plant also had a darker red leaf color than all other plants in the population. Selection for a slower bolting red leaf type with a heavy plant type continued through the F8 generation which was trialed as a baby leaf product.

Cultivar SCARAMANGA is a red leaf lettuce similar to lettuce cultivars Blackhawk and Showdown. While somewhat similar to Blackhawk and Showdown, Cultivar SCARAMANGA produces a leaf with less undulation and a more entire leaf margin than the varieties Blackhawk and Showdown. Its red color is similar to Blackhawk, but it has improved *Bremia lactucae* resistance. Its mildew resistance is similar to Showdown, but it is lighter in color and faster growing than Showdown, which is a benefit for winter production.

Cultivar SCARAMANGA is a year-round, mildew resistant, red-leaf lettuce variety suitable for baby-leaf salad production in coastal California, the U.S. desert southwest, northern Europe, and southern Europe. It has dark red, glossy leaf, and resistance to *Bremia lactucae* (CAI-VI/BL1-30).

Some of the criteria used to select in various generations include: *Bremia* resistance, slow bolting and red leaf color.

Lettuce cultivar SCARAIVIANGA shown uniformity and stability for the traits, as described in the following Variety Description Information. It has been self-pollinated a sufficient number of generations with careful attention to uniformity of plant type. The cultivar has been increased with continued observation for uniformity. No variant traits have been observed or are expected for agronomical important traits in lettuce cultivar SCARAMANGA.

Lettuce cultivar SCARAIVIANGA has the following morphologic and other characteristics (based primarily on data collected in California). Comparison data with similar varieties Blackhawk and Showdown are also provided. The field tests were experimental trials, under supervision of the applicant.

TABLE 1

| VARIETY DESCRIPTION INFORMATION | | | |
|---|---|---|---|
| | SCARAMANGA | Blackhawk | Showdown |
| Plant: | | | |
| Type | Cutting or gathering red leaf type | Cutting or gathering red leaf type | Cutting or gathering red leaf type |
| Seed: | | | |
| Color | White | Black | Black |
| Cotyledon to Fourth Leaf Stage: | | | |
| Shape of Cotyledones | Intermediate | Intermediate | Intermediate |
| Shape of fourth leaf | Elongated | Oval | Elongated |
| Lenght/width index of fourth leaf: L/W * 10 | 16 | 12 | 16 |
| Apical Margin | Entire | Moderately dentate | Finely dentate |
| Basal margin | Finely dentate | Crenate/Gnawed | Crenate/Gnawed |
| Undulation | Slight | Marked | Marked |

TABLE 1-continued

VARIETY DESCRIPTION INFORMATION

|  | SCARAMANGA | Blackhawk | Showdown |
|---|---|---|---|
| Antocyanin distribution | Margin only | Margin only | Margin only |
| Antocyanin concentration | Intense | Intense | Intense |
| Antocyanin Roling | Absent | Present | Present |
| Cupping | Slight | Slight | Markedly |
| Reflexing | None | Apical margin | Lateral Margin |
| Mature Leaves: | | | |
| Margin incision depth | Absent/Shallow | Moderate | Absent/Shallow |
| Margin indentation | Entire | Shallowly dentate | Crenate |
| Undulation of the apical margin | Moderate | Strong | Strong |
| Antocyanin distribution | Throughout | Throughout | na |
| Antocyanin concentration | Intense | Intense | Intense |
| Size | Large | Medium | Small |
| Glossiness | Glossy | Moderate | Moderate |
| Blistering | Moderate | Strong | Moderate |
| Leaf Thickness | Thin | Thick | Intermediate |
| Trichromes | Absent | Present | present |
| Plant: | | | |
| Spread of frame leaves | 29 cm | 31 cm | 29 cm |
| Head Diameter | 27 cm | 28 cm | 26 cm |
| Head weight | 200 g | 155 g | 70 g |
| Core: | | | |
| Diameter at Base of Head | 23 mm | 13 mm | na |
| Ratio of head diameter/core diameter | 1.2 | 2.2 | na |
| Core height from base of head to apex | 67 mm | 43 mm | na |
| Bolting (first water date June 21st) | | | |
| Number of days from first water date to seed stalk emergence in summer conditions | 70 | 54 | 45 |
| Height of mature seed stalk | 115 cm | 112 cm | 80 cm |
| Spread of bolter plant | 46 cm | 38 cm | 35 cm |
| Bolter leaves | Straight | Curved | Curved |
| Margin | Entire | Dentate | Dentate |
| Bolter habit: terminal inflorescence | Present | Present | Present |
| Bolter habit: lateral shoots | Present | Present | Present |
| Bolter habit: basal side shoots | Absent | Absent | Absent |
| Bremia resistance | | | |
| European Isolates | Bl1-30 | Bl1-16, 19, 21, 23 | BL1-31 |
| California Isolates | CA I-VI | CA I-VI | CA I-VIII |

Lettuce cultivar GIMLET has superior characteristics and was developed from an initial cross that was made in a greenhouse in Gilroy, Calif. during the first year of development under number 710600116, between two experimental *Lactuca sativa* plants. The F$_1$ plants were grown in Gilroy, Calif. F2 plants were highly heterogeneous and phenotypic selection only started at the F3 generation for plants showing *Bremia* resistance. F3 were selected for *Bremia* resistance. The F4 plant was a red leaf plant, similar to the Blackhawk variety but glossier and less blistered. Subsequence generations were selected for the plant, with increasing levels of uniformity, up to the F8 generation.

Cultivar GIMLET is a red leaf lettuce similar to lettuce cultivars Blackhawk and Shockwave. While somewhat similar to Blackhawk and Shockwave, Cultivar GIMLET has smoother and more glossy leaf that the two other varieties. Resistance to *Bremia* is also improved, Blackhawk being resistant to CA I-VI/Bl1-16, 19, 21, 23 and Shockwave being resistant to CA I-VI/Bl1-25 and 27 while GIMLET is resistant to CA I-VIII/Bl1-26 and 28. Further, Cultivar GIMLET is slower to bolt than either of Blackhawk and Shockwave Cultivar GIMLET is a year-round, mildew resistant, red-leaf lettuce variety suitable for baby-leaf salad production in coastal California, the U.S. desert southwest, northern Europe, and southern Europe. It has dark red, glossy leaf, and resistance to *Bremia lactucae* (CAI-VIII:BL1-26 and 28).

Some of the criteria used to select in various generations include: *Bremia* resistance, slow bolting and red leaf color.

Cultivar GIMLET has shown uniformity and stability for the traits, as described in the following Variety Description Information. It has been self-pollinated a sufficient number of generations with careful attention to uniformity of plant type. The cultivar has been increased with continued observation for uniformity. No variant traits have been observed or are expected for agronomical important traits in lettuce cultivar GIMLET.

Lettuce cultivar GIMLET the following morphologic and other characteristics (based primarily on data collected in California). Comparison date with similar varieties Blackhawk and Shockwave are also provided. The field tests were experimental trials, under supervision of the applicant.

TABLE 2

VARIETY DESCRIPTION INFORMATION

| | GIMLET | Blackhawk | Shockwave |
|---|---|---|---|
| Plant: | | | |
| Type | Cutting or gathering red leaf type | Cutting or gathering red leaf type | Cutting or gathering red leaf type |
| Seed: | | | |
| Color | White | Black | White |
| Cotyledon to Fourth Leaf Stage: | | | |
| Shape of Cotyledones | Intermediate | Intermediate | Intermediate |
| Shape of fourth leaf | Elongated | Oval | Elongated |
| Lenght/width index of fourth leaf: L/W * 10 | 18 | 12 | 16 |
| Apical Margin | Entire | Moderately dentate | Finely dentate |
| Basal margin | Entire | Crenate/Gnawed | Coarsely dentate |
| Undulation | Medium | Marked | Medium |
| Antocyanin distribution | Throughtout | Throughtout | Throughtout |
| Antocyanin concentration | Intense | Intense | Intense |
| Antocyanin Roling | Absent | Present | Present |
| Cupping | Slight | Slight | Slight |
| Reflexing | None | Apical margin | Lateral Margin |
| Mature Leaves: | | | |
| Margin incision depth | Absent/Shallow | Moderate | Moderate |
| Margin indentation | Entire | Shallowly dentate | Crenate |
| Undulation of the apical margin | Moderate | Strong | Moderate |
| Antocyanin distribution | Throughout | Throughout | Throughout |
| Antocyanin concentration | Intense | Intense | Intense |
| Size | Small | Medium | Medium |
| Glossiness | Glossy | Moderate | Moderate |
| Blistering | Absent | Strong | Moderate |
| Leaf Thickness | Thin | Thick | Intermediate |
| Trichromes | Absent | Present | present |
| Plant: | | | |
| Spread of frame leaves | 19 cm | 31 cm | 33 cm |
| Head Diameter | 19 cm | 26 cm | 28 cm |
| Head weight | 65 g | 155 g | 145 g |
| Core: | | | |
| Diameter at Base of Head | 13 mm | 13 mm | 14 mm |
| Ratio of head diameter/core diameter | 1.5 | 2 | 2 |
| Core height from base of head to apex | 50 mm | 43 mm | 45 mm |
| Bolting (first water date June 21st) | | | |
| Number of days from first water date to seed stalk emergence in summer conditions | 70 | 54 | 64 |
| Height of mature seed stalk | 86 cm | 112 cm | 81 cm |
| Spread of bolter plant | 31 cm | 38 cm | 40 cm |
| Bolter leaves | Curved | Curved | Curved |
| Margin | Entire | Dentate | Dentate |
| Bolter habit: terminal inflorescence | Present | Present | Present |
| Bolter habit: lateral shoots | Present | Present | Present |
| Bolter habit: basal side shoots | Absent | Absent | Absent |
| Bremia resistance | | | |
| European Isolates | Bl1-26, 28 | Bl1-16, 19, 21, 23 | Bl1-25, 27 |
| California Isolates | CA I-VIII | CA I-VI | CA I-VI |

Lettuce cultivar SPRITZER has superior characteristics and was developed from an initial cross that was made in a greenhouse in Gilroy, Calif. during the first year of development under number 71040276, between two experimental *Lactuca sativa* plants, one being a red tango lettuce, the other one being an iceberg lettuce. The $F_1$ plants were grown in Gilroy, Calif. F2 plants were highly heterogeneous due to the wide original cross and it took 11 generations of inbreeding to achieve the cultivar SPRITZER, selection criteria at each generation focusing on a tango leaf shape, leaf thickness and dark, red color.

Cultivar SPRITZER is a red tango lettuce similar to lettuce cultivars Asilomar and Intrepid. While somewhat similar to Asilomar and Intrepid, Cultivar SPRITZER has more curled, tango-like leaf leaves than either both of which are classified as red oak-leaf varieties. smoother and more glossy leaf that the two other varieties. Further, Cultivar SPRITZER is faster to bolt than either of Asilomar and Intrepid. Cultivar SPRITZER has also white seed color while Asilomar and Intrepid have black seed color.

Cultivar SPRITZER is a year-round, mildew resistant, red-tango lettuce variety suitable for baby-leaf salad production in coastal California, the U.S. desert southwest, northern Europe, and southern Europe. It has resistance to *Bremia lactucae* (CAI-VIII/BL1-25, 27-28 and 30-31).

Some of the criteria used to select in various generations include: *bremia* resistance, tango leaf shape, leaf thickness and dark, red color.

Cultivar SPRITZER has shown uniformity and stability for the traits, as described in the following Variety Description Information. It has been self-pollinated a sufficient number of generations with careful attention to uniformity of plant type. The cultivar has been increased with continued observation for uniformity. No variant traits have been observed or are expected for agronomical important traits in lettuce cultivar SPRITZER.

Lettuce cultivar SPRITZER has the following morphologic and other characteristics (based primarily on data collected in California). Comparison date with similar varieties Asilomar and Intrepid are also provided. The field tests were experimental trials, under supervision of the applicant.

TABLE 3

VARIETY DESCRIPTION INFORMATION

|  | SPRITZER | Asilomar | Intrepid |
|---|---|---|---|
| Plant: | | | |
| Type | Red Tango | Red oak | Red oak |
| Seed: | | | |
| Color | White | Black | Black |
| Cotyledon to Fourth Leaf Stage: | | | |
| Shape of Cotyledones | Intermediate | Intermediate | Intermediate |
| Shape of fourth leaf | Pinnately lobed | Pinnately lobed | Pinnately lobed |
| Lenght/width index of fourth leaf: L/W * 10 | 12 | 17 | 16 |
| Apical Margin | Entire | Crenate/Gnawed | Entire |
| Basal margin | Lobed | Lobed | Lobed |
| Undulation | Medium | Medium | Medium |
| Antocyanin distribution | Throughtout | Throughtout | Throughtout |
| Antocyanin concentration | Intense | Intense | Intense |
| Antocyanin Roling | Absent | Absent | Absent |
| Cupping | Uncupped | Slight | Uncupped |
| Reflexing | None | None | None |
| Mature Leaves: | | | |
| Margin incision depth | Deep | Deep | Deep |
| Margin indentation | Shallowly dentate | Deeply dentate | Shallowly dentate |
| Undulation of the apical margin | Strong | Strong | Strong |
| Antocyanin distribution | Throughout | Throughout | Throughout |
| Antocyanin concentration | Intense | Intense | Intense |
| Size | Medium | Medium | Medium |
| Glossiness | Moderate | Dull | Moderate |
| Blistering | Absent | Absent | Absent |
| Leaf Thickness | Thin | Intermediate | Thin |
| Trichromes | Absent | Absent | Absent |
| Plant: | | | |
| Spread of frame leaves | 18 cm | 26 cm | 33 cm |
| Head Diameter | 16 cm | 24 cm | 30 cm |
| Head weight | 100 g | 120 g | 180 g |
| Core: | | | |
| Diameter at Base of Head | 16 mm | 18 mm | 15 mm |
| Ratio of head diameter/core diameter | 1 | 1.3 | 2 |
| Core height from base of head to apex | 73 mm | 45 mm | 65 mm |
| Bolting (first water date June 21st) | | | |
| Number of days from first water date to seed stalk emergence in summer conditions | 56 | 66 | 65 |
| Height of mature seed stalk | 102 cm | 89 cm | 70 cm |
| Spread of bolter plant | 28 cm | 36 cm | 21 cm |
| Bolter leaves | Straight | Curved | Curved |
| Margin | Dentate | Dentate | Dentate |
| Bolter habit: terminal inflorescence | Present | Present | Present |
| Bolter habit: lateral shoots | Present | Present | Present |
| Bolter habit: basal side shoots | Absent | Absent | Absent |
| Bremia resistance | | | |
| European Isolates | Bl1-25, 27-28, 30-31 | BL1-31 | BL1-31 |
| California Isolates | CA I-VIII | CA I-VIII | CA I-VIII |

Lettuce cultivar MOJITO has superior characteristics and was developed from an initial cross that was made in a greenhouse in Gilroy, Calif. during the first year of development under number 71040051, between two experimental *Lactuca sativa* plants, one being a red tango lettuce, the other one being an iceberg lettuce. The $F_1$ plants were grown in Gilroy, Calif. F2 plants were highly heterogeneous due to the wide original cross and it took 10 generations of inbreeding to achieve the cultivar MOJITO, selection criteria at each generation focusing on a tango leaf shape, leaf thickness and dark, green color.

Cultivar MOJITO is a tango lettuce similar to lettuce cultivars Flurry and Tango. While somewhat similar to Flurry and Tango, Cultivar MOJITO has darker, narrower, less undulated leaf and higher levels or resistance to *Bremia lactucae*.

Cultivar MOJITO is a year-round, mildew resistant, red-tango lettuce variety suitable for baby-leaf salad production in coastal California, the U.S. desert southwest, northern Europe, and southern Europe. It has resistance to *Bremia lactucae* (CAI-VIII/BL1-26, 28 and 31).

Some of the criteria used to select in various generations include: *Bremia* resistance, tango leaf shape, leaf thickness and dark, green color.

Cultivar MOJITO has shown uniformity and stability for the traits, as described in the following Variety Description Information. It has been self-pollinated a sufficient number of generations with careful attention to uniformity of plant type. The cultivar has been increased with continued observation for uniformity. No variant traits have been observed or are expected for agronomical important traits in lettuce cultivar MOJITO.

Lettuce cultivar r MOJITO has the following morphologic and other characteristics (based primarily on data collected in California). Comparison date with similar varieties Flurry and Tango are also provided. The field tests were experimental trials, under supervision of the applicant.

TABLE 4

| VARIETY DESCRIPTION INFORMATION | | | |
|---|---|---|---|
| | MOJITO | Flurry | Tango |
| Plant: | | | |
| Type | Tango | Tango | Tango |
| Seed: | | | |
| Color | Black | Black | Black |
| Cotyledon to Fourth Leaf Stage: | | | |
| Shape of Cotyledones | Intermediate | Intermediate | Intermediate |
| Shape of fourth leaf | Elongated | Pinnately lobed | Pinnately lobed |
| Lenght/width index of fourth leaf: L/W * 10 | 9 | 14 | 15 |
| Apical Margin | Lobed | Coarsely dentate | Lobed |
| Basal margin | Moderately dentate | Entire | Lobed |
| Undulation | Slight | Marked | Marked |
| Green color | Medium green | Light green | Medium green |
| Antocyanin distribution | Absent | Absent | Absent |
| Antocyanin Roling | Absent | Absent | Present |
| Cupping | Uncupped | Slight | Markedly |
| Reflexing | None | None | Lateral Margins |
| Mature Leaves: | | | |
| Margin incision depth | Deep | Deep | Deep |
| Margin indentation | Deeply dentate | Deeply dentate | Deeply dentate |
| Undulation of the apical margin | Strong | Strong | Strong |
| Green color | Medium green | Light green | Medium green |
| Antocyanin distribution | Absent | Absent | Absent |
| Size | Medium | Medium | Medium |
| Glossiness | Moderate | Moderate | Moderate |
| Blistering | Absent | Absent | Moderate |
| Leaf Thickness | Intermediate | Thick | Intermediate |
| Trichromes | Absent | Absent | Present |
| Plant: | | | |
| Spread of frame leaves | 23 cm | 19 cm | 20 cm |
| Head Diameter | 21 cm | 18 cm | 19 cm |
| Head weight | 115 g | 130 g | 60 g |
| Butt: | | | |
| Midrib | Moderately raised | Flattened | Moderately raised |
| Core: | | | |
| Diameter at Base of Head | 20 mm | 16 mm | 19 mm |
| Ratio of head diameter/core diameter | 1.1 | 1.2 | 1 |
| Core height from base of head to apex | 60 mm | 41 mm | 29 mm |
| Bolting (first water date June 21st) | | | |
| Number of days from first water date to seed stalk emergence in summer conditions | 57 | 59 | 33 |
| Height of mature seed stalk | 102 cm | 95 cm | 137 cm |
| Spread of bolter plant | 30 cm | 34 cm | 30 cm |
| Bolter leaves | Straight | Straight | Curved |

TABLE 4-continued

VARIETY DESCRIPTION INFORMATION

| | MOJITO | Flurry | Tango |
|---|---|---|---|
| Margin | Dentate | Dentate | Dentate |
| Color | Medium green | Medium green | Medium green |
| Bolter habit: terminal inflorescence | Present | Present | Present |
| Bolter habit: lateral shoots | Present | Present | Present |
| Bolter habit: basal side shoots | Absent | Absent | Absent |
| Bremia resistance | | | |
| European Isolates | Bl1-26, 28, 31 | BL1-17, 19, 21-23, 25, 27, 30-31 | None claimed |
| California Isolates | CA I-VIII | CA I-VIII | None claimed |

Further Embodiments of the Invention

This invention also is directed to methods for producing a lettuce plant by crossing a first parent lettuce plant with a second parent lettuce plant wherein either the first or second parent lettuce plant is a lettuce plant of the line SCARAIVIANGA, GIMLET, SPRITZER and/or MOJITO. Further, both first and second parent lettuce plants can come from cultivar SCARAMANGA, GIMLET, SPRITZER and/or MOJITO, respectively. When self-pollinated, or crossed with another lettuce cultivar SCARAIVIANGA plant, the lettuce cultivar SCARAMANGA will be stable, while when crossed with another, different lettuce cultivar plant, an $F_1$ hybrid seed is produced. When self-pollinated, or crossed with another lettuce cultivar GIMLET plant, the lettuce cultivar GIMLET will be stable, while when crossed with another, different lettuce cultivar plant, an $F_1$ hybrid seed is produced. When self pollinated, or crossed with another lettuce cultivar SPRITZER plant, the lettuce cultivar SPRITZER will be stable, while when crossed with another, different lettuce cultivar plant, an $F_1$ hybrid seed is produced When self-pollinated, or crossed with another lettuce cultivar MOJITO plant, the lettuce cultivar MOJITO will be stable, while when crossed with another, different lettuce cultivar plant, an $F_1$ hybrid seed is produced. Such methods of hybridization and self-pollination of the lettuce are well known to those skilled in the art of lettuce breeding. See, for example, F. A. Bliss, 1980, Common Bean, In Hybridization of Crop Plants, Fehr and Hadley, eds., Chapter 17: 273-284, American Society of Agronomy and Crop Science Society of America, Publishers.

Still further, this invention also is directed to methods for producing an SCARAMANGA-derived lettuce plant by crossing cultivar SCARAMANGA with a second lettuce plant and growing the progeny seed, and repeating the crossing and growing steps with the cultivar SCARAMANGA-derived plant from 0 to 7 times. Thus, any such methods using the cultivar SCARAMANGA are part of this invention: selfing, backcrosses, hybrid production, crosses to populations, and the like. All plants produced using cultivar SCARAMANGA as a parent are within the scope of this invention, including plants derived from cultivar SCARAMANGA. Advantageously, the cultivar is used in crosses with other, different, cultivars to produce first generation ($F_1$) lettuce seeds and plants with superior characteristics.

Still further, this invention also is directed to methods for producing an GIMLET-derived lettuce plant by crossing cultivar GIMLET with a second lettuce plant and growing the progeny seed, and repeating the crossing and growing steps with the cultivar GIMLET-derived plant from 0 to 7 times. Thus, any such methods using the cultivar GIMLET are part of this invention: selfing, backcrosses, hybrid production, crosses to populations, and the like. All plants produced using cultivar GIMLET as a parent are within the scope of this invention, including plants derived from cultivar GIMLET. Advantageously, the cultivar is used in crosses with other, different, cultivars to produce first generation ($F_1$) lettuce seeds and plants with superior characteristics.

Still further, this invention also is directed to methods for producing an SPRITZER-derived lettuce plant by crossing cultivar SPRITZER with a second lettuce plant and growing the progeny seed, and repeating the crossing and growing steps with the cultivar SPRITZER-derived plant from 0 to 7 times. Thus, any such methods using the cultivar SPRITZER are part of this invention: selfing, backcrosses, hybrid production, crosses to populations, and the like. All plants produced using cultivar SPRITZER as a parent are within the scope of this invention, including plants derived from cultivar SPRITZER. Advantageously, the cultivar is used in crosses with other, different, cultivars to produce first generation ($F_1$) lettuce seeds and plants with superior characteristics.

Still further, this invention also is directed to methods for producing an MOJITO-derived lettuce plant by crossing cultivar MOJITO with a second lettuce plant and growing the progeny seed, and repeating the crossing and growing steps with the cultivar MOJITO-derived plant from 0 to 7 times. Thus, any such methods using the cultivar MOJITO are part of this invention: selfing, backcrosses, hybrid production, crosses to populations, and the like. All plants produced using cultivar MOJITO as a parent are within the scope of this invention, including plants derived from cultivar MOJITO. Advantageously, the cultivar is used in crosses with other, different, cultivars to produce first generation ($F_1$) lettuce seeds and plants with superior characteristics.

The invention is also directed to a method of producing a lettuce plant derived from the lettuce SCARAMANGA, the method comprising the steps of: (a) preparing a progeny plant derived from SCARAMANGA, by crossing a plant of SCARAMANGA with a second lettuce plant; (b) crossing the progeny plant thereof with itself or a second lettuce plant to produce a seed of a progeny plant of a subsequent generation; (c) growing a progeny plant of a subsequent generation from said seed and crossing the progeny plant of a subsequent generation with itself or a second lettuce plant; and (d) repeating step b) or c) for at least 1 more generation to produce a lettuce plant derived from the lettuce SCARAMANGA.

The invention is also directed to a method of producing a lettuce plant derived from the lettuce GIMLET, the method comprising the steps of: (a) preparing a progeny plant derived from GIMLET, by crossing a plant of GIMLET with a second lettuce plant; (b) crossing the progeny plant thereof with itself or a second lettuce plant to produce a seed of a progeny plant of a subsequent generation; (c) growing a progeny plant of a subsequent generation from said seed and crossing the progeny plant of a subsequent generation with itself or a second lettuce plant; and (d) repeating step b) or c) for at least 1 more generation to produce a lettuce plant derived from the lettuce GIMLET.

The invention is also directed to a method of producing a lettuce plant derived from the lettuce SPRITZER, the method comprising the steps of: (a) preparing a progeny plant derived from SPRITZER by crossing a plant of SPRITZER with a second lettuce plant; (b) crossing the progeny plant thereof with itself or a second lettuce plant to produce a seed of a progeny plant of a subsequent generation; (c) growing a progeny plant of a subsequent generation from said seed and crossing the progeny plant of a subsequent generation with itself or a second lettuce plant; and (d) repeating step b) or c) for at least 1 more generation to produce a lettuce plant derived from the lettuce SPRITZER.

The invention is also directed to a method of producing a lettuce plant derived from the lettuce MOJITO, the method comprising the steps of: (a) preparing a progeny plant derived from MOJITO, by crossing a plant of MOJITO with a second lettuce plant; (b) crossing the progeny plant thereof with itself or a second lettuce plant to produce a seed of a progeny plant of a subsequent generation; (c) growing a progeny plant of a subsequent generation from said seed and crossing the progeny plant of a subsequent generation with itself or a second lettuce plant; and (d) repeating step b) or c) for at least 1 more generation to produce a lettuce plant derived from the lettuce MOJITO.

As used herein, the term "plant" includes plant cells, plant protoplasts, plant cell tissue cultures from which lettuce plants can be regenerated, plant calli, plant clumps and plant cells that are intact in plants or parts of plants, such as embryos, pollen, ovules, flowers, seeds, heads, stems, roots, anthers, pistils, root tips, leaves, meristematic cells, axillary buds and the like.

As is well-known in the art, tissue culture of lettuce can be used for the in vitro regeneration of a lettuce plant. Tissue culture of various tissues of lettuce and regeneration of plants therefrom is well known and widely published. For example, reference may be had to Teng et al., *HortScience*, 27: 9, 1030-1032 (1992), Teng et al., *HortScience*. 28: 6, 669-671 (1993), Zhang et al., *Journal of Genetics and Breeding*, 46: 3, 287-290 (1992), Webb et al., *Plant Cell Tissue and Organ Culture*, 38: 1, 77-79 (1994), Curtis et al., *Journal of Experimental Botany*, 45: 279, 1441-1449 (1994), Nagata et al., *Journal for the American Society for Horticultural Science*, 125: 6, 669-672 (2000). Thus, it is clear from the literature that the state of the art is such that these methods of obtaining plants are routinely used and have a very high rate of success. Thus, another aspect of this invention is to provide cells which upon growth and differentiation produce lettuce plants having the physiological and morphological characteristics of lettuce cultivars of the present application.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, leaves, stems, roots, root tips, anthers, pistils, meristematic cells, axillary buds and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques, the disclosures of which are incorporated herein by reference.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes." Over the last fifteen to twenty years several methods for producing transgenic plants have been developed and the present invention, in particular embodiments, also relates to transformed versions of the claimed cultivar.

Plant transformation involves the construction of an expression vector which will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid and can be used alone or in combination with other plasmids to provide transformed lettuce plants using transformation methods as described below to incorporate transgenes into the genetic material of the lettuce plant(s).

Expression Vectors for Lettuce Transformation: Marker Genes

Expression vectors include at least one genetic marker operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Fraley, et al., *Proc. Natl. Acad. Sci. USA*, 80:4803 (1983). Another commonly used selectable marker gene is the hygromycin phosphotransferase gene which confers resistance to the antibiotic hygromycin. Vanden Elzen, et al., *Plant Mol. Biol.*, 5:299 (1985).

Additional selectable marker genes of bacterial origin that confer resistance to antibiotics include gentamycin acetyl transferase, streptomycin phosphotransferase and aminoglycoside-3'-adenyl transferase, the bleomycin resistance determinant (Hayford, et al., *Plant Physiol.*, 86:1216 (1988); Jones, et al., *Mol. Gen. Genet.*, 210:86 (1987); Svab, et al., *Plant Mol. Biol.*, 14:197 (1990); Hille, et al., *Plant Mol. Biol.*, 7:171 (1986)). Other selectable marker genes confer resistance to herbicides such as glyphosate, glufosinate or bromoxynil (Comai, et al., *Nature*, 317:741-744 (1985); Gordon-Kamm, et al., *Plant Cell*, 2:603-618 (1990); and Stalker, et al., *Science*, 242:419-423 (1988)).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz, et al., *Somatic Cell Mol. Genet.*, 13:67 (1987); Shah, et al., *Science*, 233:478 (1986); and Charest, et al., *Plant Cell Rep.*, 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase, and chloramphenicol acetyltransferase (Jefferson, R. A., *Plant Mol. Biol. Rep.*, 5:387 (1987); Teeri, et al., *EMBO J.*, 8:343 (1989); Koncz, et al., *Proc. Natl. Acad. Sci. USA*, 84:131 (1987); DeBlock, et al., *EMBO J.*, 3:1681 (1984)).

In vivo methods for visualizing GUS activity that do not require destruction of plant tissue are available. However, these in vivo methods for visualizing GUS activity have not proven useful for recovery of transformed cells because of low sensitivity, high fluorescent backgrounds and limitations associated with the use of luciferase genes as selectable markers.

A gene encoding Green Fluorescent Protein (GFP) has been utilized as a marker for gene expression in prokaryotic and eukaryotic cells (Chalfie, et al., *Science*, 263:802 (1994)). GFP and mutants of GFP may be used as screenable markers.

Expression Vectors for Lettuce Transformation: Promoters

Genes included in expression vectors must be driven by a nucleotide sequence comprising a regulatory element, for example, a promoter. Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in a certain tissue are referred to as "tissue-specific." A "cell-type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell-type specific, and inducible promoters constitute the class of "non-constitutive" promoters. A "constitutive" promoter is a promoter that is active under most environmental conditions.

A. Inducible Promoters—An inducible promoter is operably linked to a gene for expression in lettuce. Optionally, the inducible promoter is operably linked to a nucleotide sequence encoding a signal sequence which is operably linked to a gene for expression in lettuce. With an inducible promoter the rate of transcription increases in response to an inducing agent.

Any inducible promoter can be used in the instant invention. See, Ward, et al., *Plant Mol. Biol.*, 22:361-366 (1993). Exemplary inducible promoters include, but are not limited to, that from the ACEI system which responds to copper (Mett, et al., *Proc. Natl. Acad. Sci. USA*, 90:4567-4571 (1993)); In2 gene from maize which responds to benzenesulfonamide herbicide safeners (Gatz, et al., *Mol. Gen. Genetics*, 243:32-38 (1994)), or Tet repressor from Tn10 (Gatz, et al., *Mol. Gen. Genetics*, 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena, et al., *Proc. Natl. Acad. Sci. USA*, 88:0421 (1991)).

B. Constitutive Promoters—A constitutive promoter is operably linked to a gene for expression in lettuce or the constitutive promoter is operably linked to a nucleotide sequence encoding a signal sequence which is operably linked to a gene for expression in lettuce.

Many different constitutive promoters can be utilized in the instant invention. Exemplary constitutive promoters include, but are not limited to, the promoters from plant viruses such as the 35S promoter from CaMV (Odell, et al., *Nature*, 313:810-812 (1985)) and the promoters from such genes as rice actin (McElroy, et al., *Plant Cell* 2, 163-171 (1990)); ubiquitin (Christensen, et al., *Plant Mol. Biol.*, 12:619-632 (1989) and Christensen, et al., *Plant Mol. Biol* 18:675-689 (1992)); pEMU (Last, et al., *Theor. Appl. Genet.*, 81:581-588 (1991)); MAS (Velten, et al., *EMBO J.*, 3:2723-2730 (1984)) and maize H3 histone (Lepetit, et al., *Mol. Gen. Genetics*, 231:276-285 (1992) and Atanassova, et al., *Plant Journal*, 2 (3):291-300 (1992)). The ALS promoter, XbaI/NcoI fragment 5' to the *Brassica napus* ALS3 structural gene (or a nucleotide sequence similarity to said XbaI/NcoI fragment), represents a particularly useful constitutive promoter. See, PCT Application WO 96/30530.

C. Tissue-specific or Tissue-preferred Promoters—A tissue-specific promoter is operably linked to a gene for expression in lettuce. Optionally, the tissue-specific promoter is operably linked to a nucleotide sequence encoding a signal sequence which is operably linked to a gene for expression in lettuce. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter such as that from the phaseolin gene (Murai, et al., *Science*, 23:476-482 (1983) and Sengupta-Gopalan, et al., *Proc. Natl. Acad. Sci. USA* 82:3320-3324 (1985)); a leaf-specific and light-induced promoter such as that from cab or rubisco (Simpson, et al., *EMBO J.*, 4(11): 2723-2729 (1985) and Timko, et al., *Nature*, 318:579-582 (1985)); an anther-specific promoter such as that from LAT52 (Twell, et al., *Mol. Gen. Genetics*, 217:240-245 (1989)); a pollen-specific promoter such as that from Zm13 or a microspore-preferred promoter such as that from apg (Twell, et al., *Sex. Plant Reprod.,* 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall, or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized.

The presence of a signal sequence directs a polypeptide to either an intracellular organelle or subcellular compartment or for secretion to the apoplast. Many signal sequences are known in the art. See, for example, Becker, et al., *Plant Mol. Biol.,* 20:49 (1992); Knox, C., et al., "Structure and Organization of Two Divergent Alpha-Amylase Genes from Barley," *Plant Mol. Biol.,* 9:3-17 (1987); Lerner, et al., *Plant Physiol.,* 91:124-129 (1989); Fontes, et al., *Plant Cell,* 3:483-496 (1991); Matsuoka, et al., *Proc. Natl. Acad. Sci.,* 88:834 (1991); Gould, et al., *J. Cell. Biol.,* 108:1657 (1989); Creissen, et al., *Plant J.,* 2:129 (1991); Kalderon, et al., *Cell,* 39:499-509 (1984); Steifel, et al., "Expression of a maize cell wall hydroxyproline-rich glycoprotein gene in early leaf and root vascular differentiation," *Plant Cell,* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.,* 114:92-6 (1981).

According to a preferred embodiment, the transgenic plant provided for commercial production of foreign protein is a lettuce plant. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see *Methods in Plant Molecular Biology and Biotechnology,* Glick and Thompson Eds., CRC Press, Inc., Boca Raton, 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR, and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

Plant disease resistance genes. Plant defenses are often activated by specific interaction between the product of a disease resistance gene (R) in the plant and the product of a corresponding avirulence (Avr) gene in the pathogen. A plant variety can be transformed with one or more cloned resistance genes to engineer plants that are resistant to specific pathogen strains. See, for example, Jones, et al., *Science,* 266:789 (1994) (cloning of the tomato Cf-9 gene for resistance to *Cladosporium fulvum*); Martin, et al., *Science,* 262:1432 (1993) (tomato Pto gene for resistance to *Pseudomonas syringae* pv. tomato encodes a protein kinase); Mindrinos, et al., *Cell,* 78:1089 (1994) (*Arabidopsis* RSP2 gene for resistance to *Pseudomonas syringae*).

B. A *Bacillus thuringiensis* protein, a derivative thereof or a synthetic polypeptide modeled thereon. See, for example, Geiser, et al., *Gene,* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995, and 31998.

C. A lectin. See, for example, Van Damme, et al., *Plant Molec. Biol.,* 24:25 (1994), who disclose the nucleotide sequences of several *Clivia miniata* mannose-binding lectin genes.

D. A vitamin-binding protein such as avidin. See, PCT Application US 93/06487 which teaches the use of avidin and avidin homologues as larvicides against insect pests.

E. An enzyme inhibitor, for example, a protease or proteinase inhibitor or an amylase inhibitor. See, for example, Abe, et al., *J. Biol. Chem.,* 262:16793 (1987) (nucleotide sequence of rice cysteine proteinase inhibitor); Huub, et al., *Plant Molec. Biol.,* 21:985 (1993) (nucleotide sequence of cDNA encoding tobacco proteinase inhibitor I); Sumitani, et al., *Biosci. Biotech. Biochem.,* 57:1243 (1993) (nucleotide sequence of *Streptomyces nitrosporeus* α-amylase inhibitor).

F. An insect-specific hormone or pheromone such as an ecdysteroid or juvenile hormone, a variant thereof, a mimetic based thereon, or an antagonist or agonist thereof. See, for example, the disclosure by Hammock, et al., *Nature,* 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosure of Pratt, et al., *Biochem. Biophys. Res. Comm.,* 163:1243 (1989) (an allostatin is identified in *Diploptera puntata*). See also, U.S. Pat. No. 5,266,317 to Tomalski, et al., which discloses genes encoding insect-specific, paralytic neurotoxins.

H. An insect-specific venom produced in nature by a snake, a wasp, etc. For example, see Pang, et al., *Gene,* 116:165 (1992), for disclosure of heterologous expression in plants of a gene coding for a scorpion insectotoxic peptide.

An enzyme responsible for a hyperaccumulation of a monoterpene, a sesquiterpene, a steroid, hydroxamic acid, a phenylpropanoid derivative or another non-protein molecule with insecticidal activity.

J. An enzyme involved in the modification, including the post-translational modification, of a biologically active molecule, for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See, PCT Application WO 93/02197 (Scott, et al.), which discloses the nucleotide sequence of a callase gene. DNA molecules which contain chitinase-encoding sequences can be obtained, for example, from the ATCC under Accession Nos. 39637 and 67152. See also, Kramer, et al., *Insect Biochem. Molec. Biol.*, 23:691 (1993), who teach the nucleotide sequence of a cDNA encoding tobacco hornworm chitinase, and Kawalleck, et al., *Plant Molec. Biol.*, 21:673 (1993), who provide the nucleotide sequence of the parsley ubi4-2 polyubiquitin gene.

K. A molecule that stimulates signal transduction. For example, see the disclosure by Botella, et al., *Plant Molec. Biol.*, 24:757 (1994), of nucleotide sequences for mung bean calmodulin cDNA clones, and Griess, et al., *Plant Physiol.*, 104:1467 (1994), who provide the nucleotide sequence of a maize calmodulin cDNA clone.

L. A hydrophobic moment peptide. See, PCT Application WO 95/16776, which discloses peptide derivatives of tachyplesin which inhibit fungal plant pathogens, and PCT Application WO 95/18855, which teaches synthetic antimicrobial peptides that confer disease resistance.

M. A membrane permease, a channel former, or a channel blocker. For example, see the disclosure of Jaynes, et al., *Plant Sci*, 89:43 (1993), of heterologous expression of a cecropin-β lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., *Ann. Rev. Phytopathol.*, 28:451 (1990). Coat protein-mediated resistance has been conferred upon transformed plants against alfalfa mosaic virus, cucumber mosaic virus and tobacco streak virus, potato virus X, potato virus Y, tobacco etch virus, tobacco rattle virus, and tobacco mosaic virus. Id.

O. An insect-specific antibody or an immunotoxin derived therefrom. Thus, an antibody targeted to a critical metabolic function in the insect gut would inactivate an affected enzyme, killing the insect.

P. A virus-specific antibody. See, for example, Tavladoraki, et al., *Nature*, 366:469 (1993), who show that transgenic plants expressing recombinant antibody genes are protected from virus attack.

Q. A developmental-arrestive protein produced in nature by a pathogen or a parasite. Thus, fungal endo-α-1, 4-D-polygalacturonases facilitate fungal colonization and plant nutrient release by solubilising plant cell wall homo-α-1,4-D-galacturonase. See, Lamb, et al., *Bio/Technology*, 10:1436 (1992).

R. A developmental-arrestive protein produced in nature by a plant. For example, Logemann, et al., *Bio/Technology*, 10:305 (1992), have shown that transgenic plants expressing the barley ribosome-inactivating gene have an increased resistance to fungal disease.

S. Genes involved in the Systemic Acquired Resistance (SAR) Response and/or the pathogenesis-related genes. Briggs, S., "Plant disease resistance. Grand unification system theory in sight," *Current Biology*, 5(2) (1995).

T. Antifungal genes. See, Cornelissen and Melchers, "Strategies for Control of Fungal Diseases with Transgenic Plants," *Plant Physiol.*, 101:709-712 (1993); and Bushnell, et al., "Genetic Engineering of Disease Resistance in Cereal," *Can. J. of Plant Path.*, 20(2):137-149 (1998).

2. Genes that Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee, et al., *EMBO J.*, 7:1241 (1988), and Miki, et al., *Theor. Appl. Genet.*, 80:449 (1990), respectively.

B. Glyphosate (resistance conferred by mutant 5-enolpyruvlshikimate-3-phosphate synthase (EPSPS) and aroA genes, respectively) and other phosphono compounds such as glufosinate (phosphinothricin acetyl transferase (PAT) and *Streptomyces hygroscopicus* PAT bar genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. A DNA molecule encoding a mutant aroA gene can be obtained under ATCC Accession No. 39256, and the nucleotide sequence of the mutant gene is disclosed in U.S. Pat. No. 4,769,061 to Comai. European Patent Application No. 0 333 033 to Kumada, et al., and U.S. Pat. No. 4,975,374 to Goodman, et al., disclose nucleotide sequences of glutamine synthetase genes which confer resistance to herbicides such as L-phosphinothricin. See also, Russel, D. R., et al., *Plant Cell Report*, 12:3 165-169 (1993). The nucleotide sequence of a phosphinothricin-acetyl-transferase (PAT) gene is provided in European Application No. 0 242 246 to Leemans, et al. DeGreef, et al., *Bio/Technology*, 7:61 (1989) describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop, are the Acc1-S1, Acc1-S2, and Acc2-S3 genes described by Marshall, et al., *Theor. Appl. Genet.*, 83:435 (1992).

C. An herbicide that inhibits photosynthesis, such as a triazine (psbA and gs+ genes) and a benzonitrile (nitrilase gene). Przbila, et al., *Plant Cell*, 3:169 (1991), describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC Accession Nos. 53435, 67441, and 67442. Cloning and expression of DNA coding for a glutathione S-transferase is described by Hayes, et al., *Biochem. J.*, 285:173 (1992).

D. Acetohydroxy acid synthase, which has been found to make plants that express this enzyme resistant to multiple types of herbicides, has been introduced into a variety of plants. See, Hattori, et al., "An Acetohydroxy acid synthase mutant reveals a single site involved in multiple herbicide resistance," *Mol. Gen. Genet.*, 246:419-425 (1995). Other genes that confer tolerance to herbicides include a gene encoding a chimeric protein of rat cytochrome P4507A1 and yeast NADPH-cytochrome P450 oxidoreductase (Shiota, et al., "Herbicide-resistant Tobacco Plants Expressing the Fused Enzyme between Rat Cytochrome P4501A1 (CYP1A1) and Yeast NADPH-Cytochrome P450 Oxidoreductase," *Plant Physiol.*, 106:17 (1994)), genes for glutathione reductase and superoxide dismutase (Aono, et al., "Paraquat tolerance of transgenic *Nicotiana tabacum* with enhanced activities of glutathione reductase and superoxide dismutase," *Plant Cell Physiol.*, 36:1687 (1995)), and genes for various phosphotransferases (Datta, et al., "Herbicide-resistant Indica rice plants from IRRI breeding line IR72 after PEG-mediated transformation of protoplants," *Plant Mol. Biol.*, 20:619 (1992).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306, 6,282,837, 5,767,373, and International Publication WO 01/12825.

3. Genes that Confer or Contribute to a Value-Added Trait, Such as:

Increased iron content of the lettuce, for example by transforming a plant with a soybean ferritin gene as described in Goto et al., *Acta Horticulturae*, 521, 101-109 (2000). Parallel to the improved iron content enhanced growth of transgenic lettuce was also observed in early development stages.

B. Decreased nitrate content of leaves, for example by transforming a lettuce plant with a gene coding for a nitrate reductase. See for example Curtis et al., *Plant Cell Report*, 18: 11, 889-896 (1999).

C. Increased sweetness of the lettuce by transferring a gene coding for monellin that elicits a flavor 100,000 times sweeter than sugar on a molar basis. See Penarrubia et al., *Biotechnology*, 10: 5, 561-564 (1992).

D. Delayed senescence or browning by transferring a gene or acting on the transcription of a gene involved in the plant senescence. See Wang et al. *In Plant Mol. Bio*, 52:1223-1235 (2003) on the role of the deoxyhypusine synthase in the senescence. See also U.S. Pat. No. 6,538,182 issued Mar. 25, 2003.

Methods for Lettuce Transformation

Numerous methods for plant transformation have been developed including biological and physical plant transformation protocols. See, for example, Miki, et al., "Procedures for Introducing Foreign DNA into Plants," in *Methods in Plant Molecular Biology and Biotechnology*, Glick and Thompson Eds., CRC Press, Inc., Boca Raton, pp. 67-88 (1993). In addition, expression vectors and in-vitro culture methods for plant cell or tissue transformation and regeneration of plants are available. See, for example, Gruber, et al., "Vectors for Plant Transformation" in *Methods in Plant Molecular Biology and Biotechnology*, Glick and Thompson Eds., CRC Press, Inc., Boca Raton, pp. 89-119 (1993).

*Agrobacterium*-mediated Transformation—One method for introducing an expression vector into plants is based on the natural transformation system of *Agrobacterium*. See, for example, Horsch, et al., *Science*, 227:1229 (1985); Diant, et al., *Molecular Breeding*, 3:1, 75-86 (1997). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.*, 10:1 (1991). Descriptions of *Agrobacterium* vector systems and methods for *Agrobacterium*-mediated gene transfer are provided by Gruber, et al., supra, Miki, et al., supra, and Moloney, et al., *Plant Cell Reports*, 8:238 (1989). See also, U.S. Pat. No. 5,591,616 issued Jan. 7, 1997.

B. Direct Gene Transfer—Despite the fact the host range for *Agrobacterium*-mediated transformation is broad, some cereal or vegetable crop species and gymnosperms have generally been recalcitrant to this mode of gene transfer, even though some success has been achieved in rice and corn. Hiei, et al., *The Plant Journal*, 6:271-282 (1994) and U.S. Pat. No. 5,591,616 issued Jan. 7, 1997. Several methods of plant transformation, collectively referred to as direct gene transfer, have been developed as an alternative to *Agrobacterium*-mediated transformation. A generally applicable method of plant transformation is microprojectile-mediated transformation where DNA is carried on the surface of microprojectiles measuring 1 to 4 microns. The expression vector is introduced into plant tissues with a biolistic device that accelerates the microprojectiles to speeds of 300 to 600 m/s which is sufficient to penetrate plant cell walls and membranes. Russell, D. R., et al., *Pl. Cell. Rep.*, 12, 165-169 (3 Jan. 1993); Aragao, F. J. L., et al., *Plant Mol. Biol.*, 20, 357-359 (2 Oct. 1992); Aragao, *Theor. Appl. Genet.*, 93:142-150 (1996); Kim, J.; Minamikawa, T., *Plant Science*, 117:131-138 (1996); Sanford, et al., *Part. Sci. Technol.*, 5:27 (1987); Sanford, J. C., *Trends Biotech.*, 6:299 (1988); Klein, et al., *Bio/Tech.*, 6:559-563 (1988); Sanford, J. C., *Physiol Plant*, 7:206 (1990); Klein, et al., *Biotechnology*, 10:268 (1992).

Another method for physical delivery of DNA to plants is sonication of target cells. Zhang, et al., *Bio/Technology*, 9:996 (1991). Alternatively, liposome and spheroplast fusion have been used to introduce expression vectors into plants. Deshayes, et al., *EMBO J.*, 4:2731 (1985); Christou, et al., *Proc Natl. Acad. Sci. USA*, 84:3962 (1987). Direct uptake of DNA into protoplasts using $CaCl_2$ precipitation, polyvinyl alcohol or poly-L-ornithine have also been reported. Hain, et al., *Mol. Gen. Genet.*, 199:161 (1985) and Draper, et al., *Plant Cell Physiol.*, 23:451 (1982). Electroporation of protoplasts and whole cells and tissues have also been described Saker, M. and Kuhne, T., Biologia *Plantarum*, 40(4):507-514 (1997/98); D'Halluin, et al., *Plant Cell*, 4:1495-1505 (1992); and Spencer, et al., *Plant Mol. Biol.*, 24:51-61 (1994)).

Following transformation of lettuce target tissues, expression of the above-described selectable marker genes allows for preferential selection of transformed cells, tissues and/or plants, using regeneration and selection methods well known in the art.

The foregoing methods for transformation would typically be used for producing a transgenic variety. The transgenic variety could then be crossed with another (non-transformed or transformed) variety in order to produce a new transgenic variety. Alternatively, a genetic trait that has been engineered into a particular lettuce line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties that do not contain that gene. As used herein, "crossing" can refer to a simple X by Y cross or the process of backcrossing depending on the context.

Backcrossing

When the term lettuce plant, cultivar or lettuce line are used in the context of the present invention, this also includes cultivars where one or more desired traits has been introduced through backcrossing methods, whether such trait is a naturally occurring one or a transgenic one. Backcrossing methods can be used with the present invention to improve or introduce a characteristic into the line. The term "backcrossing" as used herein refers to the repeated crossing of a hybrid progeny back to the recurrent parent, i.e., backcrossing one, two, three, four, five, six, seven, eight, nine, or more times to the recurrent parent. The parental lettuce plant which contributes the gene for the desired characteristic is termed the nonrecurrent or donor parent. This terminology refers to the fact that the nonrecurrent parent is used one time in the backcross protocol and therefore does not recur. The parental lettuce plant to which the gene or genes from the nonrecurrent parent are transferred is known as the recurrent parent as it is used for several rounds in the backcrossing protocol.

In a typical backcross protocol, the original cultivar of interest (recurrent parent) is crossed to a second line (nonrecurrent parent) that carries the gene or genes of interest to be transferred. The resulting progeny from this cross are then crossed again to the recurrent parent and the process is repeated until a lettuce plant is obtained wherein essentially all of the desired morphological and physiological characteristics of the recurrent parent are recovered in the converted plant, generally determined at a 5% significance level when grown in the same environmental condition, in addition to the gene or genes transferred from the nonrecurrent parent. It has to be noted that some, one, two, three, or more, self-pollination and growing of population might be included between two successive backcrosses. Indeed, an appropriate selection in the population produced by the self-pollination, i.e., selection for the desired trait and physiological and morphological characteristics of the recurrent parent might be equivalent to one, two or even three, additional backcrosses in a continuous series without rigorous selection, saving time, money and effort to the breeder. A non limiting example of such a protocol would be the following: (a) the first generation $F_1$ produced by the cross of the recurrent parent A by the donor parent B is backcrossed to parent A; (b) selection is practiced for the plants having the desired trait of parent B; (c) selected plants are self-pollinated to produce a population of plants where selection is practiced for the plants having the desired trait of parent B and the physiological and morphological characteristics of parent A; (d) the selected plants are backcrossed one, two, three, four, five, six, seven, eight, nine, or more times to parent A to produce selected backcross progeny plants comprising the desired trait of parent B and the physiological and morphological characteristics of parent A. Step (c) may or may not be repeated and included between the backcrosses of step (d).

The selection of a suitable recurrent parent is an important step for a successful backcrossing procedure. The goal of a backcross protocol is to alter or substitute a single trait or characteristic in the original line. To accomplish this, a gene or genes of the recurrent cultivar is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross, one of the major purposes is to add some commercially desirable, agronomical important trait to the plant. The exact backcrossing protocol will depend on the characteristic or trait being altered to determine an appropriate testing protocol. Although backcrossing methods are simplified when the characteristic being transferred is a single gene and dominant allele, multiple genes and recessive allele(s) may also be transferred and therefore, backcross breeding is by no means restricted to character(s) governed by one or a few genes. In fact the number of genes might be less important than the identification of the character(s) in the segregating population. In this instance it may then be necessary to introduce a test of the progeny to determine if the desired characteristic(s) has been successfully transferred. Such tests encompass visual inspection, simple crossing but also follow up of the characteristic(s) through genetically associated markers and molecular assisted breeding tools. For example, selection of progeny containing the transferred trait is done by direct selection, visual inspection for a trait associated with a dominant allele, while the selection of progeny for a trait that is transferred via a recessive allele requires selfing the progeny to determine which plant carries the recessive allele(s).

Many single gene traits have been identified that are not regularly selected for in the development of a new line but that can be improved by backcrossing techniques. Single gene traits may or may not be transgenic. An example of a gene controlling resistance to the lettuce leaf aphid *Nasonovia ribisnigri* (Nr gene) can be found in Van der Arend and Schijndel in *Breeding for Resistance to insects and Mites*, IOBC wprs Bulletin 22(10), 35-43 (1999). These genes are generally inherited through the nucleus. Some other single gene traits are described in U.S. Pat. Nos. 5,777,196, 5,948, 957, and 5,969,212, the disclosures of which are specifically hereby incorporated by reference.

In 1981 the backcross method of breeding accounted for 17% of the total breeding effort for inbred corn line development in the United States, according to, Hallauer, A. R., et al., "Corn Breeding," Corn and Corn Improvement, No. 18, pp. 463-481 (1988).

The backcross breeding method provides a precise way of improving varieties that excel in a large number of attributes but are deficient in a few characteristics. (Page 150 of the Pr. R. W. Allard's 1960 book, *Principles of Plant Breeding*, published by John Wiley & Sons, Inc.) The method makes use of a series of backcrosses to the variety to be improved during which the character or the characters in which improvement is sought is maintained by selection. At the end of the backcrossing the gene or genes being transferred unlike all other genes, will be heterozygous. Selfing after the last backcross produces homozygosity for this gene pair(s) and, coupled with selection, will result in a variety with exactly the adaptation, yielding ability, and quality characteristics of the recurrent parent but superior to that parent in the particular characteristic(s) for which the improvement program was undertaken. Therefore, this method provides the plant breeder with a high degree of genetic control of his work.

The backcross method is scientifically exact because the morphological and agricultural features of the improved variety could be described in advance and because the same variety could, if it were desired, be bred a second time by retracing the same steps (Briggs, "Breeding wheats resistant to bunt by the backcross method," *Jour. Amer. Soc. Agron.*, 22:289-244 (1930)).

Backcrossing is a powerful mechanism for achieving homozygosity and any population obtained by backcrossing must rapidly converge on the genotype of the recurrent parent. When backcrossing is made the basis of a plant breeding program, the genotype of the recurrent parent will be modified only with regards to genes being transferred, which are maintained in the population by selection.

Successful backcrosses are, for example, the transfer of stem rust resistance from 'Hope' wheat to 'Bart' wheat and even pursuing the backcrosses with the transfer of bunt resistance to create 'Bart 38', having both resistances. Also highlighted by Allard is the successful transfer of mildew, leaf spot and wilt resistances in 'California Common' alfalfa to create 'Caliverde'. This new 'Caliverde' variety produced through the backcross process is indistinguishable from 'California Common' except for its resistance to the three named diseases.

One of the advantages of the backcross method is that the breeding program can be carried out in almost every environment that will allow the development of the character being transferred.

The backcross technique is not only desirable when breeding for disease resistance but also for the adjustment of morphological characters, color characteristics, and simply inherited quantitative characters, such as earliness, plant height, and seed size and shape. In this regard, a medium grain type variety, 'Calady', has been produced by Jones and Davis. As dealing with quantitative characteristics, they selected the donor parent with the view of sacrificing some of the intensity of the character for which it was chosen, i.e., grain size. 'Lady Wright', a long grain variety was used as the donor parent and 'Coloro', a short grain variety as the recurrent parent. After four backcrosses, the medium grain type variety 'Calady' was produced.

DEPOSIT INFORMATION

A deposit of the lettuce seeds of this invention is maintained by Shamrock Seed Company Inc., 3 Harris Place, Salinas, Calif. 93901-4593 USA. In addition, a sample of the lettuce seeds of this invention has been deposited with the National Collections of Industrial, Food and Marine Bacteria (NCIMB), 23 St Machar Drive, Aberdeen, Scotland, AB24 3RY, United Kingdom.

To satisfy the enablement requirements of 35 U.S.C. 112, and to certify that the deposit of the isolated strain of the present invention meets the criteria set forth in 37 CFR 1.801-1.809, Applicants hereby make the following statements regarding the deposited lettuce cultivar GIMLET (deposited as NCIMB Accession No. 42639):

1. During the pendency of this application, access to the invention will be afforded to the Commissioner upon request;
2. Upon granting of the patent the strain will be available to the public under conditions specified in 37 CFR 1.808;
3. The deposit will be maintained in a public repository for a period of 30 years or 5 years after the last request or for the enforceable life of the patent, whichever is longer;
4. The viability of the biological material at the time of deposit will be tested; and
5. The deposit will be replaced if it should ever become unavailable.

Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, all restrictions on the availability to the public of the variety will be irrevocably removed by affording access to a deposit of at least 2,500 seeds of the same variety with the NCIMB.

The foregoing detailed description has been given for clearness of understanding only and no unnecessary limitations should be understood there from as modifications will be obvious to those skilled in the art.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A seed of lettuce cultivar designated GIMLET, wherein a representative sample of seed of said cultivar has been deposited under NCIMB No. 42639.

2. A lettuce plant, or a part thereof, produced by growing the seed of claim 1.

3. A lettuce plant, or a part thereof, having all the physiological and morphological characteristics of lettuce cultivar GIMLET listed in Table 2.

4. A lettuce plant, or a part thereof, having the physiological and morphological characteristics of lettuce cultivar GIMLET, wherein a representative sample of seed of said cultivar has been deposited under NCIMB No. 42639.

5. A tissue culture of regenerable cells produced from the plant of claim 2 wherein said cells of the tissue culture are produced from a plant part selected from the group consisting of embryos, meristematic cells, leaves, pollen, root, root tips, stems, anther, pistils, axillary buds, flowers and seeds.

6. A lettuce plant regenerated from the tissue culture of claim 5, said plant having the morphological and physiological characteristics of lettuce cultivar GIMLET, wherein a representative sample of seed has been deposited under NCIMB No. 42639.

7. A method for producing a lettuce seed comprising crossing a first parent lettuce plant with a second parent lettuce plant and harvesting the resultant hybrid lettuce seed, wherein said first parent lettuce plant or second parent lettuce plant is the lettuce plant of claim 2.

8. An F1 hybrid lettuce seed produced by the method of claim 7.

9. A method for producing an herbicide resistant plant comprising transforming the lettuce plant of claim 2 with a transgene that confers herbicide resistance to an herbicide selected from the group consisting of imidazolinone, sulfonylurea, glyphosate, glufosinate, L-phosphinothricin, triazine, and benzonitrile.

10. An herbicide resistant lettuce plant, or a part thereof, produced by the method of claim 9, wherein the lettuce plant, or a part thereof comprises the transgene.

11. A method for producing an insect resistant lettuce plant comprising transforming the lettuce plant of claim 2 with a transgene that confers insect resistance.

12. An insect resistant lettuce plant, or a part thereof, produced by the method of claim 11, wherein the lettuce plant, or a part thereof comprises the transgene.

13. A method for producing a disease resistant lettuce plant comprising transforming the lettuce plant of claim 2 with a transgene that confers disease resistance.

14. A disease resistant lettuce plant, or a part thereof, produced by the method of claim 13, wherein the lettuce plant, or a part thereof comprises the transgene.

15. A method of introducing a desired trait into lettuce cultivar GIMLET comprising:
   (a) crossing a lettuce cultivar GIMLET plant grown from lettuce cultivar GIMLET seed, wherein a representative sample of seed has been deposited under NCIMB No. 42639, with another lettuce plant that comprises a desired trait to produce $F_1$ progeny plants, wherein the desired trait is selected from the group consisting of insect resistance, disease resistance, water stress tolerance, heat tolerance, improved shelf life, delayed senescence, and improved nutritional quality;
   (b) selecting one or more progeny plants that have the desired trait to produce selected progeny plants;
   (c) crossing the selected progeny plants with the lettuce cultivar GIMLET plants to produce backcross progeny plants;
   (d) selecting for backcross progeny plants that have the desired trait and physiological and morphological characteristics of lettuce cultivar GIMLET listed in Table 2 to produce selected backcross progeny plants; and
   (e) repeating steps (c) and (d) three or more times in succession to produce selected fourth or higher backcross progeny plants that comprise the desired trait and the physiological and morphological characteristics of lettuce cultivar GIMLET listed in Table 2.

16. A lettuce plant produced by the method of claim 15, wherein the plant has the desired trait and the physiological and morphological characteristics of lettuce cultivar GIMLET listed in Table 2.

17. A method for producing lettuce cultivar GIMLET seed comprising crossing a first parent lettuce plant with a second parent lettuce plant and harvesting the resultant lettuce seed, wherein both said first and second lettuce plants are the lettuce plant of claim 4.

18. The lettuce plant of claim 16, wherein the desired trait is herbicide resistance and the resistance is conferred to an herbicide selected from the group consisting of imidazolinone, sulfonylurea, glyphosate, glufosinate, L-phosphinothricin, triazine, and benzonitrile.

19. The lettuce plant of claim 16, wherein the desired trait is insect resistance and the insect resistance is conferred by a transgene encoding a *Bacillus thuringiensis* endotoxin.

20. The lettuce plant of claim 16, wherein the desired trait is selected from the group consisting of insect resistance, disease resistance, water stress tolerance, heat tolerance, improved shelf life, delayed senesence, and improved nutritional quality.

21. A lettuce head, produced by growing the seed of claim 1.

22. A method of producing a lettuce plant derived from the lettuce GIMLET, the method comprising the steps of:
 (a) preparing a progeny plant derived from GIMLET by crossing the plant of claim 2 with a second lettuce plant;
 (b) crossing the progeny plant with itself or a second lettuce plant to produce a seed of a progeny plant of a subsequent generation;
 (c) growing a progeny plant of a subsequent generation from said seed and crossing the progeny plant of a subsequent generation with itself or a second lettuce plant; and
 (d) repeating step b) or c) for at least 1 more generation to produce a lettuce plant derived from the lettuce GIMLET.

* * * * *